United States Patent
Shang et al.

(10) Patent No.: US 9,833,424 B2
(45) Date of Patent: Dec. 5, 2017

(54) APPLICATION OF FLUOXETINE TO TREATMENT OF DEPIGMENTATION DISEASES

(71) Applicant: SHANDONG RUNZE PHARMACEUTICALS CO., LTD., Heze, Shandong (CN)

(72) Inventors: Jing Shang, Nanjing (CN); Liangliang Zhou, Nanjing (CN); Huali Wu, Nanjing (CN); Jia Zhou, Nanjing (CN); Yu Jin, Nanjing (CN); Sha Liao, Nanjing (CN)

(73) Assignee: SHANDONG RUNZE PHARMACEUTICALS CO., LTD., Heze (CN)

( * ) Notice: Subject to any disclaimer, the term of this patent is extended or adjusted under 35 U.S.C. 154(b) by 0 days.

(21) Appl. No.: 15/156,943

(22) Filed: May 17, 2016

(65) Prior Publication Data

US 2016/0256419 A1    Sep. 8, 2016

Related U.S. Application Data

(63) Continuation-in-part of application No. 14/364,037, filed as application No. PCT/CN2012/085929 on Dec. 5, 2012, now abandoned.

(30) Foreign Application Priority Data

Dec. 7, 2011    (CN) .......................... 2011 1 0403173

(51) Int. Cl.
    *A61K 31/138*    (2006.01)
    *A61K 9/06*    (2006.01)
    *A61K 9/00*    (2006.01)

(52) U.S. Cl.
    CPC .......... *A61K 31/138* (2013.01); *A61K 9/0014* (2013.01); *A61K 9/0053* (2013.01); *A61K 9/06* (2013.01)

(58) Field of Classification Search
    CPC .................................................. A61K 31/138
    See application file for complete search history.

(56) References Cited

U.S. PATENT DOCUMENTS

2006/0039882 A1    2/2006    Demitz et al.
2010/0092454 A1    4/2010    De Vivo et al.

FOREIGN PATENT DOCUMENTS

CN    101668526 A    3/2010

OTHER PUBLICATIONS

Hann, S. ("Particular Clinical Characteristics of Segmental Vitiligo," Vitiligo. Eds. Mauro Picardo and Alain Taïeb. Springer Berlin Heidelberg, 2010, pp. 296-298. Print.).*
Lee et al.; "The Incidence of Leukotrichia in Segmental Vitiligo: Implication of Poor Response to Medical Treatment" Int. J. Dermatol., Aug. 2011, vol. 50(8), pp. 925-927.
Ghafourian et al., "Vitiligo: symptoms, pathogenesis and treatment" International Journal of Immunopathology & Pharmacology, Oct. 2014, vol. 27(4), pp. 485-489.
Nieuwpoort et al., "Tyrosine-induced melanogenesis shows differences in morphologic and melanogenic preferences of melanosomes from light and dark skin types" Journal of Investigative Dermatology, 2004, vol. 122(5), pp. 1251-1255.
Hearing et al., "Enzymatic control of pigmentation in mammals" Faseb Journal Official Publication of the Federation of American Societies for Experimental Biology, 1991, vol. 5(14), pp. 2902-2909.
Wang et al., "The macrophage: a new factor in UVR-induced melanomagenesis" Journal of Investigative Dermatology, 2013, vol. 133(7), pp. 1711-1713.
Ferguson et al., "The regulation of tyrosinase gene transcription" Pigment Cell Research, 1997, vol. 10(10), pp. 127-138.

* cited by examiner

*Primary Examiner* — Sreeni Padmanabhan
*Assistant Examiner* — Jody Karol
(74) *Attorney, Agent, or Firm* — Gokalp Bayramoglu

(57) ABSTRACT

The present disclosure provides methods and pharmaceutical compositions for treating depigmentation diseases such as vitiligo or leukoctricia. The pharmaceutical composition contains a therapeutically effective amount of fluoxetine.

3 Claims, 15 Drawing Sheets

(***P<0.001 vs control; #P<0.05, ##P<0.01, ###P<0.001 vs PTU (35h) group; data expressed as mean±SD, n=40)

($^{}$p<0.01, $^{*}$p<0.001, vs control; $^{\#}$p<0.05, $^{\#\#\#}$p<0.001, vs PTU (35h); data expressed as mean±SD (n=40))

(***P<0.001 vs control)

(*P<0.05, **P<0.01 vs control group; ##P<0.01 vs matrix group)

(**p<0.01 vs control group; ##p<0.01 vs matrix group)

(**p<0.01 vs control; #p<0.05, ##p<0.01 vs model group)

APPLICATION OF FLUOXETINE TO TREATMENT OF DEPIGMENTATION DISEASES

BACKGROUND

Technical Field

The present invention relates to the field of medicine, and particularly relates to the application of fluoxetine in the treatment of depigmentation diseases.

Background

Skin depigmentation disease is a class of common acquired hypopigmentative skin disease caused by the deficiency of skin melanocytes or the reduction and impairment of melanin synthesis function. For example, leukotrichia is a common depigmentation disease involving a wide range of people. Vitiligo is another skin depigmentation disease is vitiligo, which can be further categorized as non-segmental vitiligo (NSV) and segmental vitiligo. Vitiligo occurs throughout the world and can involve all nations, which seriously affects the patient's normal life. Currently, depigmentation skin disease is still difficult to treat and has a high relapse rate. However, the effect of the existing drugs themselves for increasing pigment on promoting pigment synthesis is not significant, and the externally applied topical drugs (e.g., Psoralen) for increasing pigment commonly used in clinic are often difficult to effectively play the role and have photosensitivity. Therefore, there is an increasingly urgent demand for the development of therapeutic drug having definite efficacy.

Fluoxetine, with a chemical name of N-methyl-γ-[4-(trifluoromethyl)phenoxy] phenylpropylamine, and what is used in clinic is fluoxetine hydrochloride, with a trade name of prozac (Prozac®), which is developed by U.S. Eli Lilly and Company, firstly marketed in 1987 in the United States, successively applied in England, France, Germany, Japan, and other countries, and registered in China in 1996 (X960445). Its molecular formula is $C_{17}H_{18}F_3NO.HCl$ and has a molecular weight of 345.79; and its hydrochloride is a white crystal and its melting point is 179° C. to 182° C. (decomposed).

The main pharmacological effect of fluoxetine lies in that it selectively inhibits the reuptake of 5-serotonin by the presynaptic membrane of the central nervous system. Therefore, it is also called as selective 5-serotonin reuptake inhibitor. Fluoxetine is well absorbed after being orally administered, and its absorption is not affected by foods. Its blood concentration reaches a peak 6 to 8 h after taking, and the half-life of its active metabolite norfluoxetine is 7 to 10 d. Renal excretion is the main route of elimination: about 80% of the drug is excreted in the urine and 15% of the drug is excreted in the stool. Fluoxetine is substantially metabolized in liver, and the liver disease can affect its elimination. It is used in clinic for adults for the treatment of depression, obsessive-compulsive disorder and bulimia nervosa, and also used for the treatment of panic disorder complicated with or without agoraphobia. Fluoxetine mainly selectively acts on 5-serotonin system, and its action on cholinergic system, adrenergic system and histamine system is very weak. Therefore, as compared with the traditional antidepressants such as tricyclic antidepressants, heterocyclic antidepressants, and monoamine oxidase inhibitors, fluoxetine is characterized by good efficacy, weak and less adverse effects, high safety, and good tolerance. Its common adverse effects are gastrointestinal discomfort and neurological disorders, such as anorexia, nausea, headache, insomnia, sweating, and the like. Although fluoxetine is widely used in clinic and has few side effects, its effects on skin pigment synthesis have never been studied.

SUMMARY

The present disclosure provides methods for treating a depigmentation disease in a mammal. The method comprises administering an effective amount of fluoxetine to a mammal in need thereof. The mammal could be a human.

The depigmentation disease is non-segmental vitiligo, segmental vitiligo, or leukotrichia. In addition, fluoxetine can be administered orally or topically to a skin surface of the mammal in form of an ointment comprising fluoxetine, i.e., fluoxetine ointment. The mass concentration of fluoxetine in the ointment may range from 0.01% to 1%. The ointment is administered once or more per day.

It is discovered that fluoxetine may promote expressions of MITF, tyrosinase (TYR), and tyrosinase-related protein 1 (TRP-1) and may enhances the activity of tyrosinase.

This disclosure also provides a pharmaceutical composition for topical application. Such a composition comprises a therapeutically effective amount of fluoxetine and one or more carrier. The mass concentration of fluoxetine in the pharmaceutical composition ranges from 0.01% to 1%.

BRIEF DESCRIPTION OF THE DRAWINGS

The disclosure will become more fully understood from the detailed description given herein below for illustration only, and thus are not limitative of the disclosure, and wherein.

DESCRIPTION OF THE INVENTION

The present invention discloses methods and pharmaceutical compositions for treating depigmentation diseases such as leukotrichia and vitiligo. Such pharmaceutical compositions comprises fluoxetine. The methods involve administering the pharmaceutical compositions to a mammal (e.g., a person) in need thereof orally, topically, sublingually, by inhalation, or by injection.

Embodiments of the inventions are disclosed below. In one embodiment, the method for treating depigmentation disease comprises administering an effective amount of fluoxetine to a patient suffering from non-segmental vitiligo, segmental vitiligo, or leukotrichia. Fluoxetine can be administered orally or topically to a skin surface of the mammal in form of an ointment comprising fluoxetine, i.e., fluoxetine ointment. The mass concentration of fluoxetine in the ointment may range from 0.01% to 1%. The ointment is administered once or more per day. Each treatment regiment lasts from one week to a month. The ointment is applied to skin affected by the depigmentation diseases, e.g., scalp for treating leukotrichia, skin patches and surrounding areas in vitiligo, etc.

In a further embodiment, the fluoxetine composition comprises a therapeutically effective amount of fluoxetine and one or more carrier. The mass concentration of fluoxetine in the pharmaceutical composition ranges from 0.01% to 1%.

The following pharmacodynamic tests and results thereof provide evidence that fluoxetine is effective in treating skin depigmentation diseases.

Figure 1:
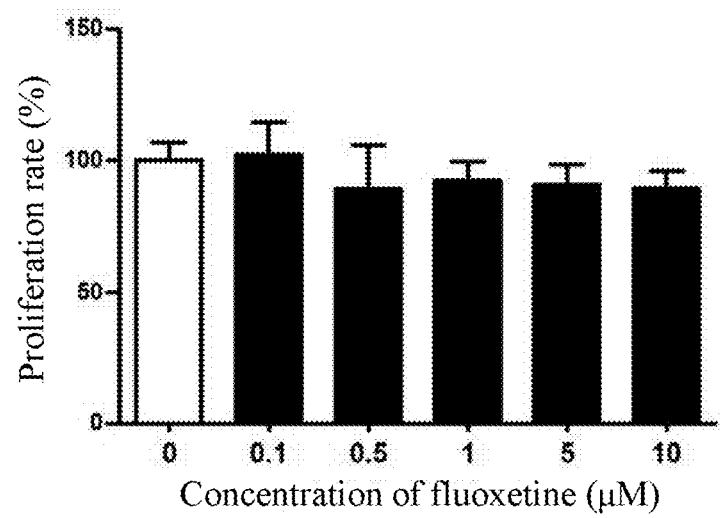
FIG. 1 shows the effect of fluoxetine on the growth of B16F10 cells.

I. Effects of Fluoxetine on Melanin Synthesis of B16F10 Mouse Melanoma Cell Line 1.1 Effects of Fluoxetine on B16F10 Cell Proliferation MTT Assay for Measuring Cell Proliferation Rate:

B16F10 cells in the exponential growth phase in good condition were taken, digested, and counted. The cells were resuspended in a high glucose DMEM culture solution containing 10% fetal bovine serum. The cells were inoculated in a 96-well culture plate with an inoculum density of $2.2 \times 10^4$ cells/ml and an inoculum size of 180 μl/well, placed in a 5% $CO_2$ incubator at 37° C., and incubated for 24 hours; fluoxetine hydrochloride with different concentrations was added at 20 μl/well, and incubated for 72 hours; 20 μl MTT per well was added, allowing reaction in an incubator at 37° C. for 4 hours; supernatant was sucked and discarded, 150 μl DMSO per well was added, the plate was shaken on a shaker for 10 minutes; the absorbance of each well was measured at a wavelength of 570 nm using a microwell plate reader, and the cell proliferation rate was calculated. The results were shown in FIG. 1.

Experimental results: compared with the blank control group, fluoxetine administration group (0.1 to 10 μM) had no significant effect on the growth of B16F10 cells (P>0.05).

Experimental conclusions: fluoxetine (0.1 to 10 μM) showed low toxicity and low carcinogenesis on B16F10 melanoma cells.

1.2 Effects of Fluoxetine on Tyrosinase Activity of B16F10 Cells.

Figure 2:
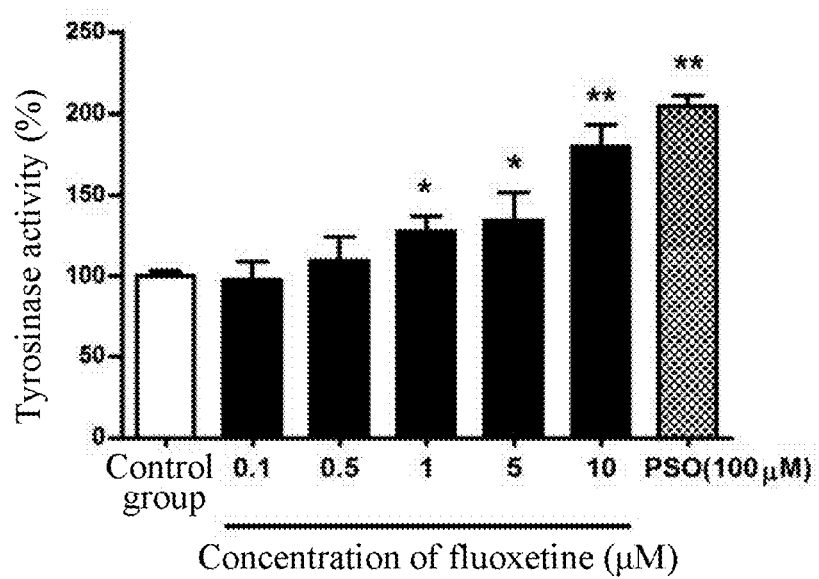
FIG. 2 shows the effect of fluoxetine on the tyrosinase activity of B16F10 cells.

L-DOPA Oxidation Assay for Measuring Tyrosinase Activity:

B16F10 cells in the exponential growth phase in good condition were taken, digested, and counted. The cells were inoculated in a 6-well plate with an inoculum concentration of $1 \times 10^5$ cells/ml and an inoculum size of 2 ml/well, placed in a 5% $CO_2$ incubator at 37° C. and incubated for 24 hours; high glucose DMEM medium containing 2.5% fetal bovine serum was used at 1.8 ml/well, fluoxetine hydrochloride with different concentrations was added at 0.2 ml/well and incubated for 72 hours; washed with PBS twice, cells were collected in doff tubes, 100 μl non-denaturing lysis solution (containing 1 nM PM SF) was added to each tube, lysed at 4° C. for 20 min, centrifuged at 4° C., at 12000 r/min for 10 min, the supernatant was taken for protein quantification (BCA method), and the protein concentration was calculated; a amount containing 30 μg protein was taken and added to a 96-well plate, added up to 100 μl with PBS (0.1 M, pH 6.8), then 0.01% L-DOPA 100 μl was added, with three independent wells for each concentration, incubated away from light at 37° C. for 60 min, and OD values were measured at a wavelength of 475 nm. The absorbance values of per μg of protein were calculated, with the results expressed in percentage. The results were shown in FIG. 2. Compared with the control group in FIG. 2, *P<0.05 and **P<0.01. PSO is psoralen.

Experimental results: compared with the blank control group, fluoxetine significantly promoted the tyrosinase activity of B16F10 cells; P<0.05 when fluoxetine was at 1 μM and 5 μM; P<0.01 when fluoxetine was at 10 μM; and the enzyme activity increase rate of fluoxetine was close to that of the positive drug psoralen when fluoxetine was in the highest concentration.

Experimental conclusions: fluoxetine had significant effects of promoting the activity of tyrosinase which is the rate-limiting enzyme for the melanin synthesis of B16F10 melanoma cells.

1.3 Effects of Fluoxetine on the Content of Melanin of B16F10 Cells.

Figure 3:
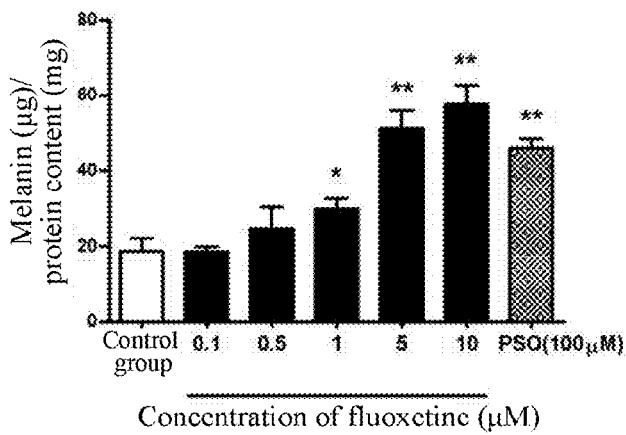
FIG. 3 shows the effect of fluoxetine on the content of melanin of B16F10 cells.

NaOH Lysis Method for the Determination of Melanin Content:

B16F10 cells in the exponential growth phase in good condition were taken, digested, and counted. The cells were inoculated in a Petri dish with a diameter of 10 cm in an inoculum size of $3\times10^5$ cells/dish, placed in 5% $CO_2$ incubator at 37° C. and incubated for 24 hours; a high glucose DMEM medium containing 2.5% fetal bovine serum was used, fluoxetine hydrochloride with different concentrations was added, incubated for 72 hours; washed with PBS twice, cells were collected, 300 µl non-denaturing lysis solution (containing 1 nM PM SF) was added, lysed at 4° C. for 20 min, centrifuged at 4° C., at 12000 r/min for 10 min, the supernatant was taken for protein quantification (BCA method), and the total protein content was calculated; 200 µl NaOH (containing 10% DMSO) was added to the lower layer of melanin pellets, placed in a water bath tank at 80° C. and lysed for two hours; a melanin content standard curve was plotted by using the melanin standard; 200 µl/well melanin which was completely dissolved was added to a 96-well plate, the absorbance values at 405 nm were measured, and the melanin content for per mg of protein was calculated. The results were shown in FIG. 3. Compared with the control group in FIG. 3, *P<0.05, **P<0.01. PSO is psoralen.

Experimental results: compared with the blank control group, fluoxetine (1 to 10 µM) significantly increased the melanin content of B16F10 cells; P<0.05 when fluoxetine was at 1 µM and P<0.01 when fluoxetine was at 5 µM and 10 µM; and the increase rate exceeded that of the positive drug psoralen.

Experimental conclusions: fluoxetine can significantly increase the melanin content of B16F10 cells.

1.4 Effects of Fluoxetine on the Expression of Proteins TYR, TRP-1, TRP-2 and MITF Which are Important for the Melanin Synthesis of B16F10 Cells.

Figure 4:
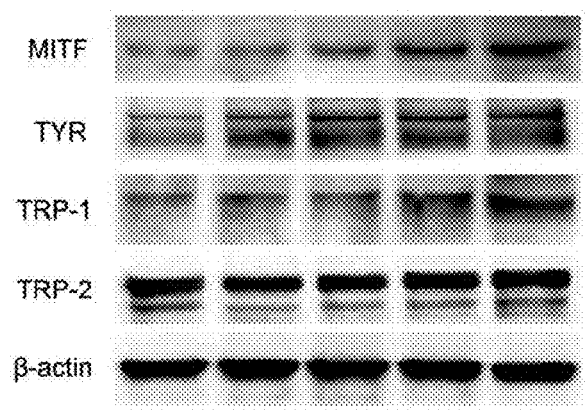
FIG. 4 shows the effect of fluoxetine on the expression of proteins MITF, TYR, TRP-1, and TRP-2, which are related to melanin synthesis of B16F10 cells.
Figure 5:
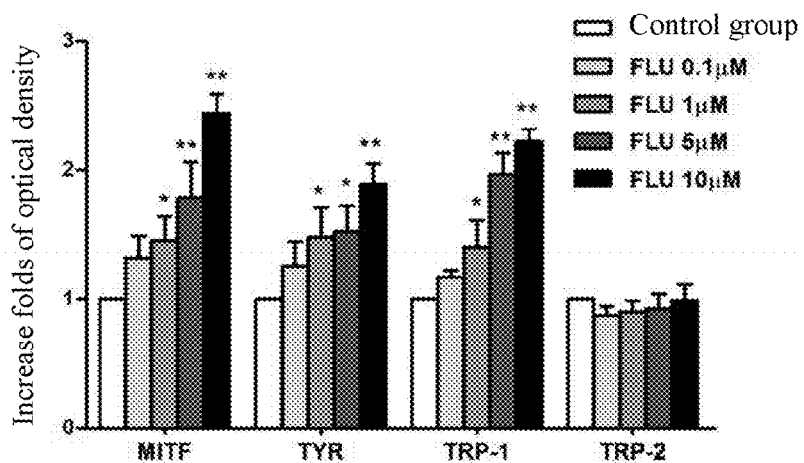
FIG. 5 shows the scanning results for the gray scales of bands with fluoxetine for the proteins MITF, TYR, TRP-1, and TRP-2, which are related to melanin synthesis of B16F10 cells.

Western Blotting Assay for Detecting the Expression of Proteins Important for the Melanin Synthesis:

B16F10 cells in the exponential growth phase in good condition were taken, digested, and counted. The cells were inoculated in a 6-well plate, grouped as above for drug treatment, cells were collected after 72 h and cell lysis solution was added, centrifuged, the supernatant was taken, the protein concentration was determined by BCA method, the protein lysis solution was adjusted to the same concentration, mixed uniformly with twice of sample-loading buffer with equal volume, boiled for 5 min, and SDS-PAGE polyacrylamide gel electrophoresis was carried out; after the electrophoresis was completed, the protein was transferred to a NC membrane with a voltage of 100 V for 1 h; blocked with TBST (0.05% Tween-20) containing 5% skimmed milk for 1 h; the membrane was incubated at 4° C. overnight respectively with primary antibodies (1:200) against TYR, TRP-1, TRP-2, MITF and β-actin which were dissolved in a blocking solution, washed with TBST 3 times with 5 min for each time; subsequently the corresponding secondary antibodies (1:4000) were added and incubated for 1 h, washed 3 times with 5 min for each time; the membrane was immersed in a prepared ECL supersensitive light-sensitive mixed liquid, with timing for 5 min, X-ray films were taken in a darkroom and the membrane was compressed to emit light; the results were obtained by developing and photographic fixing, and the results were analyzed using Quantity One Software from Bio-Rad company. The results were shown in FIG. 4 and FIG. 5. Compared with the control group in the figures, *P<0.05 and **P<0.01. FLU represents fluoxetine. Fluoxetine may also be represented by Flu, FLX, or Flx in other figures.

Experimental results: compared with the blank control group, fluoxetine can significantly improve the expression of proteins MITF, tyrosinase (TYR) and tyrosinase-related protein 1 (TRP-1) of B16F10 cells, and there was statistically significant difference. However, the protein level of tyrosinase-related protein 2 (TRP-2) was not significantly affected.

Experimental conclusions: fluoxetine can increase the melanin content through improving the expression of proteins (MITF, TYR, TRP1) which are important for the melanin synthesis of B16F10 cells.

1.5 Effects of Fluoxetine on B16F10, A375 Cell Migration

Figure 6:
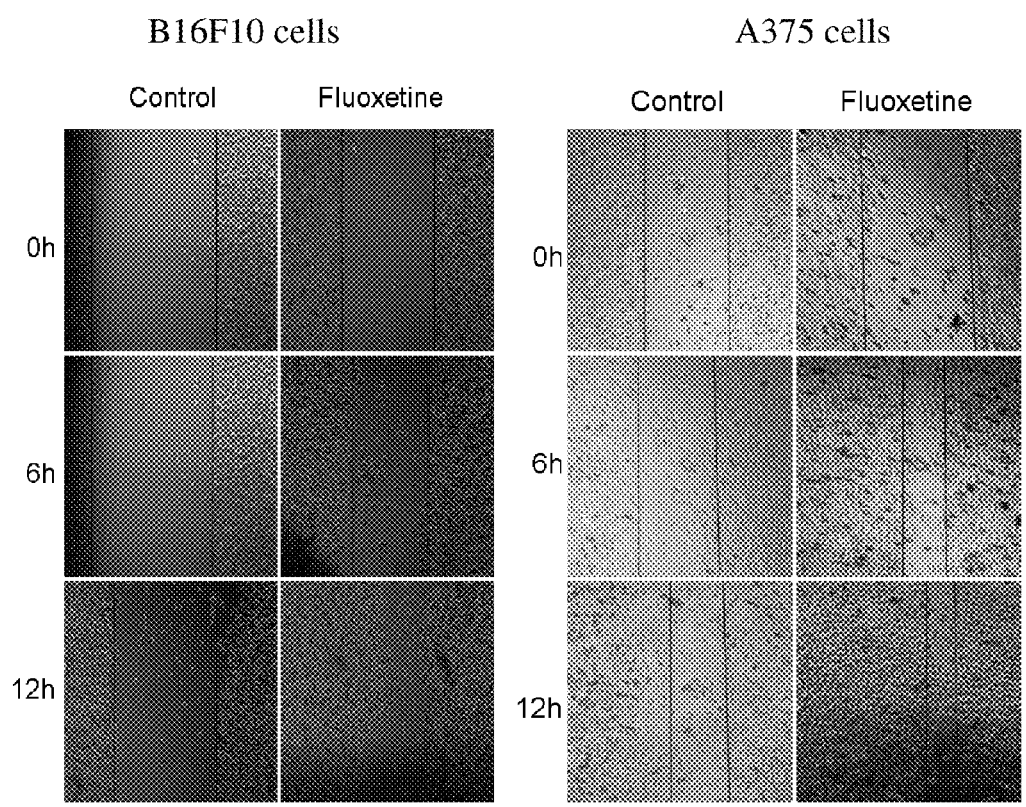
FIG. 6 shows the effect of fluoxetine on the migration of B16F10 and A375 cells (wound healing test).

FIG. 6 shows B16F10 cells and A375 cells after forty-eight (48) hours treatment with fluoxetine of concentrations in the range of 0.1-10 µM. It shows that the number of dendritic cells decreased and the cells became spindle shaped. It is believed that in the literature that melanocytes experiences cell morphogenesis into elongated shapes when migrating into keratinocytes. FIG. 6 indicates that fluoxetine may increase the mobility B16F10 and A375 cells by changing their shapes.

1.6 Effects of Fluoxetine on Primary Human Melanocytes

Figure 7:
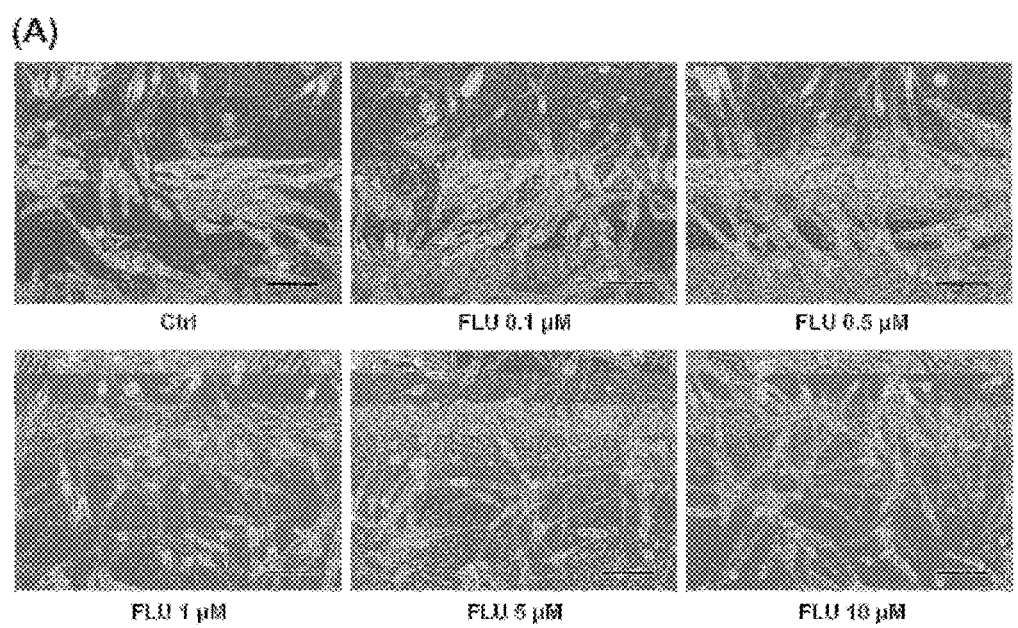
FIG. 7 shows the effect of fluoxetine on the morphology of normal human melanocytes (NHMCs).

Effects of fluoxetine on the morphology of normal human melanocytes (NHMCs). NHMCs cells were cultured with fluoxetine of concentrations ranging from 0.1-10 µM of for 5 days. Changes in dendritic morphology of NHMCs were assessed by phase-contrast microscopy. FIG. 7 shows the results at a scale bar=100 µm. As shown in FIG. 7, the control shows fewer and shorter dendrites. With increases in the dosage of fluoxetine, the number as well as the length of the primary dendritic melanocytes increase significantly.

Figure 8:
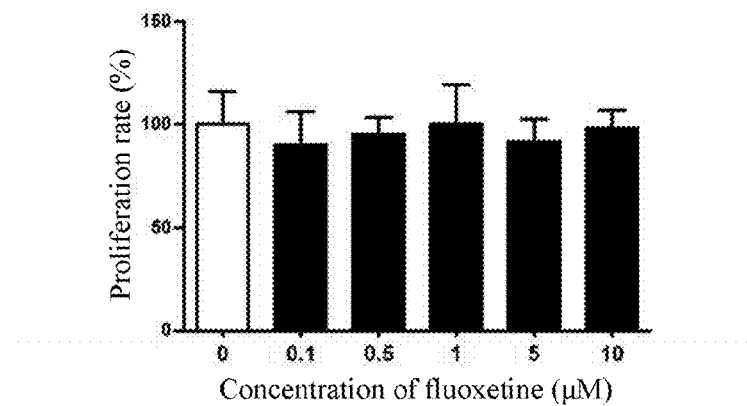
FIG. 8 shows the effect of fluoxetine on the proliferation of human primary melanocytes.

II: Effects of Fluoxetine on the Melanin Synthesis of Normal Human Primary Melanocytes 2.1 Effects of Fluoxetine on the Proliferation of Human Primary Melanocytes MTT Assay for Measuring Cell Proliferation Rate:

Normal human primary melanocytes in the exponential growth phase in good condition were taken, digested, and counted. The cells were inoculated in a 96-well culture plate with an inoculum density of $5\times10^4$ cells/ml and an inoculum size of 180 µl/well, placed in a 5% $CO_2$ incubator at 37° C., and incubated for 24 hours; fluoxetine hydrochloride with different concentrations was added and incubated for 72 hours; 20 µl MTT per well was added, allowing reaction in an incubator at 37° C. for 4 hours; supernatant was sucked and discarded, 150 µl DMSO per well was added, the plate was shaken on a shaker for 10 minutes; the absorbance of each well was measured at a wavelength of 570 nm using a microwell plate reader, and the cell proliferation rate was calculated. The results were shown in FIG. 8.

Experimental results: compared with the blank control group, fluoxetine administration group had no significant effect on the growth of normal human primary melanocytes (P>0.05).

Experimental conclusions: fluoxetine had no significant effect on the proliferation of human primary melanocytes and showed relatively low toxicity.

2.2 Effects of Fluoxetine on Tyrosinase Activity of Human Primary Melanocytes

L-DOPA Oxidation Assay for Determination of Tyrosinase Activity:

Human primary melanocytes in the exponential growth phase in good condition were taken, digested, and counted.

Figure 9:
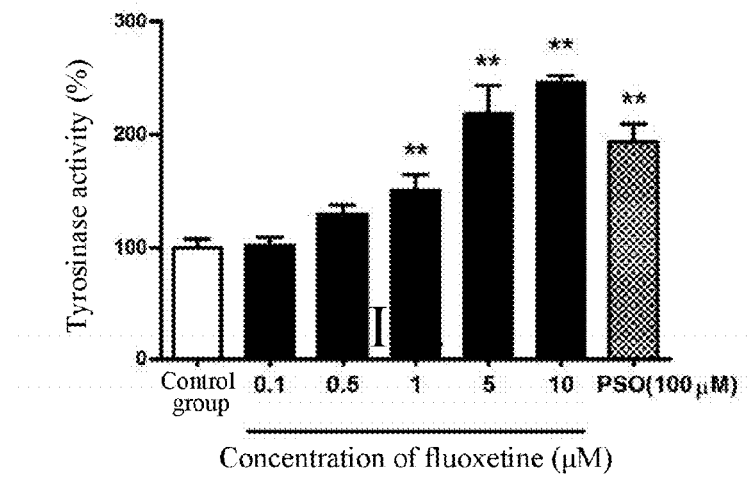
FIG. 9 shows the effect of fluoxetine on tyrosinase activity of human primary melanocytes.

The cells were inoculated in a 6-well plate with an inoculum concentration of 1×10⁵ cells/ml and an inoculum size of 2 ml/well, placed in a 5% $CO_2$ incubator at 37° C., and incubated for 24 hours; fluoxetine hydrochloride with different concentrations was added and incubated for 72 hours, washed with PBS twice, cells were collected in doff tubes, 80 μl non-denaturing lysis solution (containing 1 nM PMSF) was added to each tube, lysed at 4° C. for 20 min, centrifuged at 4° C. and 12000 r/min for 10 min, the supernatant was taken for protein quantification (BCA method), and the protein concentration was calculated; protein having a volume containing 10 μg was taken and added to a 96-well plate, added up to 100 μl with PBS (0.1 M, pH 6.8), then 0.01% L-DOPA 100 μl was added, with three wells for each concentration, incubated away from light at 37° C. for 60 min, and OD values were measured at a wavelength of 475 nm. The absorbance values of per μg of protein were calculated, with the results expressed in percentage. The results were shown in FIG. 9. Compared with the control group in FIG. 9, *$P<0.05$ and **$P<0.01$. PSO represents psoralen.

Experimental results: compared with the blank control group, fluoxetine significantly promoted the tyrosinase activity of human primary melanocytes ($P<0.01$); and the enzyme activity increase rate exceeded that of the positive drug psoralen when fluoxetine was at 5 μM and 10 μM.

Experimental conclusions: fluoxetine within the tested concentrations had significant effects of promoting the activity of tyrosinase which is the rate-limiting enzyme for the melanin synthesis of human primary melanocytes.

2.3 Effects of Fluoxetine on the Melanin Content of Human Primary Melanocytes

Figure 10:
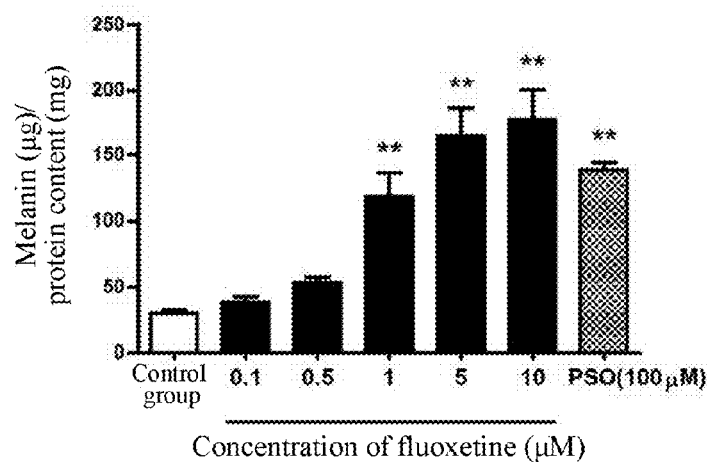
FIG. 10 shows the effect of fluoxetine on the melanin content of human primary melanocytes.

NaOH Lysis Method for Measuring Melanin Content:

Human primary melanocytes in the exponential growth phase in good condition were taken, digested, and counted. The cells were inoculated in a 6-well plate with an inoculum concentration of 1×10⁵ cells/ml and an inoculum size of 2 ml/well, placed in 5% $CO_2$ incubator at 37° C. and incubated for 24 hours; fluoxetine hydrochloride with different concentrations was added, and incubated for 72 hours; washed with PBS twice, cells were collected, 80 μl non-denaturing lysis solution (containing 1 nM PMSF) was added, lysed at 4° C. for 20 min, centrifuged at 4° C., at 12000 r/min for 10 min, the supernatant was taken for protein quantification (BCA method), and the total protein content was calculated; 100 μl NaOH (containing 10% DMSO) was added to the lower layer of melanin pellets, placed in a water bath tank at 80° C. and lysed for two hours; a melanin content standard curve was plotted by using the melanin standard; 100 μl/well melanin which was completely dissolved was added to a 96-well plate, the absorbance values at 405 nm were measured, and the melanin content for per mg of protein was calculated. The results were shown in FIG. 10. Compared with the control group in FIG. 10, *$P<0.05$ and **$P<0.01$. PSO is psoralen.

Experimental results: compared with the control group, fluoxetine significantly increased the melanin content of human primary melanocytes ($P<0.01$); and the increase rate was close to or exceeded that of the positive drug psoralen.

Experimental conclusions: fluoxetine can significantly increase the melanin content of human primary melanocytes.

2.4 Effects of Fluoxetine on the Expression of Proteins TYR, TRP-1, TRP-2 and MITF Important for the Melanin Synthesis of Human Primary Melanocytes.

Figure 11:
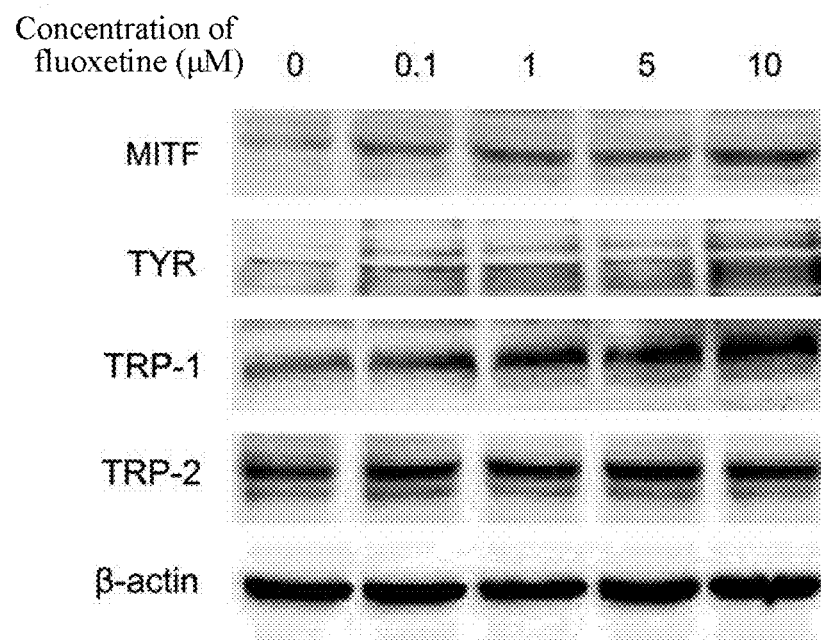
FIG. 11 shows the effect of fluoxetine on the expression of proteins MITF, TYR, TRP-1, and TRP-2, which are related to melanin synthesis of human primary melanocytes.
Figure 12:
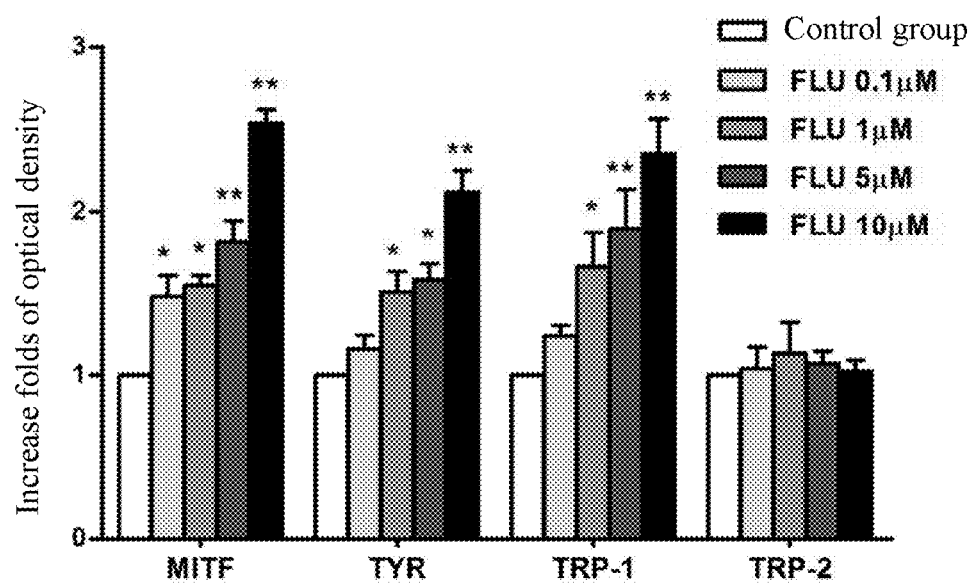
FIG. 12 shows the scanning results for the gray scales of bands with fluoxetine for the proteins MITF, TYR, TRP-1, and TRP-2, which are related to melanin synthesis of human primary melanocytes.

Western Blotting Assay for Detecting the Expression of Proteins which are Important for the Melanin Synthesis:

Human primary melanocytes in the exponential growth phase in good condition were taken, digested, and counted. The cells were inoculated in a 6-well plate, grouped as above for drug treatment, cells were collected after 72 h and cell lysis solution was added, centrifuged, the supernatant was taken, the protein concentration was determined by BCA method, the protein lysis solution was adjusted to the same concentration, mixed uniformly with twice of sample-loading buffer with equal volume, boiled for 5 min, and SDS-PAGE polyacrylamide gel electrophoresis was carried out; after the electrophoresis was completed, the protein was transferred to a NC membrane with a voltage of 100 V for 1 h, blocked with TBST (0.05% Tween-20) containing 5% skimmed milk for 1 h; the membrane was incubated at 4° C. overnight respectively with primary antibodies (1:200) against TYR, TRP-1, TRP-2, MITF and β-actin which are dissolved in blocking solution, washed with TBST 3 times with 5 min for each time; the corresponding secondary antibodies (1:4000) were added and incubated for 1 h, washed with TBST 3 times with 5 min for each time; the membrane was immersed in a prepared ECL supersensitive light-sensitive mixed liquid, with timing for 5 min, X-ray films were taken in a darkroom and the membrane was compressed to emit light; the results were obtained by developing and photographic fixing, and the results were analyzed using Quantity One Software from Bio-Rad company. The results were shown in FIG. 11 and FIG. 12. Compared with the control group, *$P<0.05$ and **$P<0.01$. FLU represents fluoxetine.

Experimental results: compared with the blank control group, fluoxetine can significantly improve the expression of proteins MITF, tyrosinase (TYR) and tyrosinase-related protein 1 (TRP-1) of human primary melanocytes, and there was statistically significant difference. However, the protein level of tyrosinase-related protein 2 (TRP-2) was not significantly affected.

Experimental conclusions: fluoxetine can increase the melanin content through improving the expression of proteins (MITF, TYR, TRP-1) which are important for the melanin synthesis of human primary melanocytes.

III Effects of Fluoxetine on the Expression of Hair Follicle Melanin and Melanin Synthesis Protein in Hair-Removed Synchronized C57BL/6 Mice.

Figure 13:
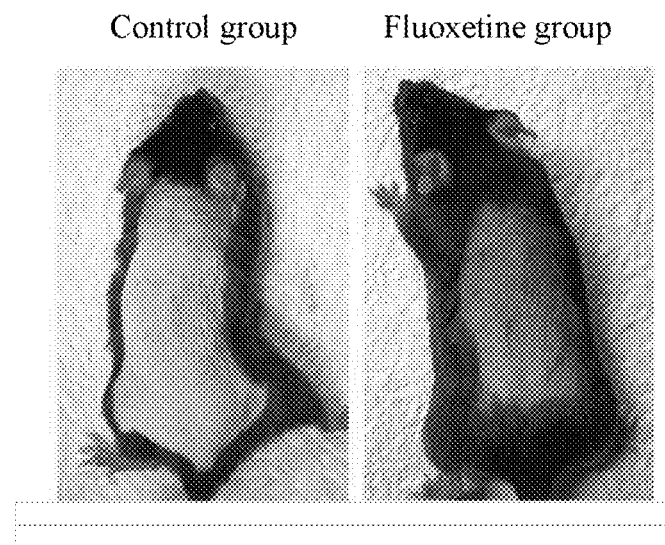
FIG. 13 shows compare skin colors on the back of C57BL/6 mice between a control and a mouse treated with fluoxetine on the 12th day after administration of fluoxetine.

3.1 Effects of Fluoxetine on Melanin Synthesis in Skin Hair Follicle of C57BL/6 Mice C57BL/6 mice was fed for acclamation, and the back hair was removed with a rosin/paraffin mixture 1 day before the experiment, to induce the synchronous growth cycle of the hair follicles. Animals were randomly divided into a solvent control group (physiological saline) and a fluoxetine administration group (20 mg/kg), with 10 animals for each group. Reference to clinical administration method was made, and gavage was performed once a day for consecutive 12 days. On the 12$^{th}$ day after administration, the condition about the skin color on the back of the mice was recorded by photographing. The results were shown in FIG. 13.

Experimental results: the pictures about the skin on the back of the mice on the 12$^{th}$ day after administration showed that the skin color in the hair-removed area of the skin of the fluoxetine administration group was significantly darkened as compared with that of the solvent control group.

Experimental conclusions: fluoxetine gavage for 12 days can significantly promote the melanin synthesis in the skin of hair-removed synchronized C57BL/6 mice.

Figure 14:
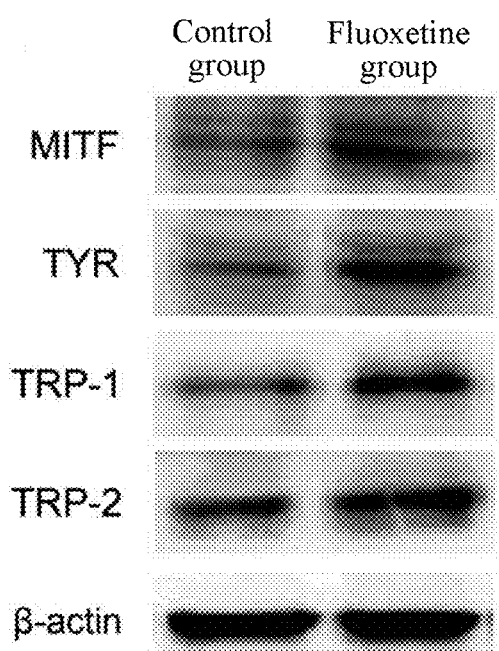
FIG. 14 shows the effect of fluoxetine on the expression of proteins MITF, TYR, TRP-1, and TRP-2 in hair follicle melanocytes of C57BL/6 mice.
Figure 15:
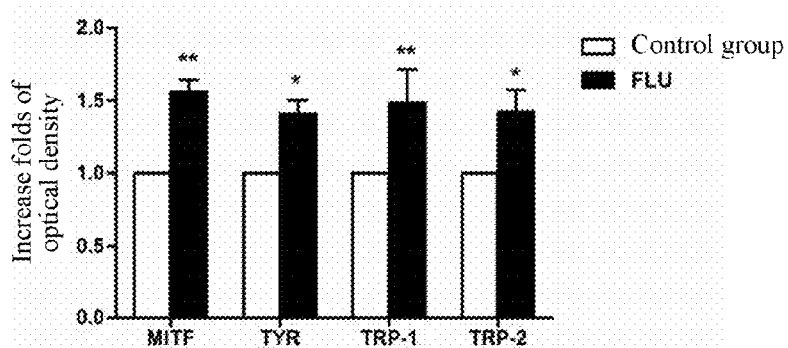
FIG. 15 shows the scanning results for the gray scales of bands with fluoxetine for MITF, TYR, TRP-1 and TRP-2 in hair follicle melanocytes of C57BL/6 mice.

3.2 Western Blotting Assay for Detecting the Expression of Proteins Important for Melanin Synthesis in Hair Follicles of C57BL/6 Mice On the 12$^{th}$ day after administration, the above animals were sacrificed to collect skin samples for Western blotting experiment. A certain amount of skin tissue of C57BL/6 mice was taken and sheared into pieces. A tissue lysis solution and a proteinase inhibitor were added. Protein was extracted after homogenization; the protein concentration was determined by BCA method, the protein lysis buffer solution was adjusted to the same concentration, mixed uniformly with twice of sample-loading buffer with equal volume, boiled for 5 min, and SDS-PAGE polyacrylamide gel electrophoresis was carried out; after the electrophoresis was completed, the protein was transferred to a NC membrane with a voltage of 100 V for 1 h, blocked with TBST (0.05% Tween-20) containing 5% skimmed milk for 1 h; the membrane was incubated at 4° C. overnight respectively with primary antibodies (1:200) against TYR, TRP-1, TRP-2, MITF and β-actin which are dissolved in blocking solution, washed with TBST 3 times with 5 min for each time; subsequently the corresponding secondary antibodies (1:4000) were added and incubated for 1 h, washed 3 times with 5 min for each time; the membrane was immersed in a prepared ECL supersensitive light-sensitive mixed liquid, with timing for 5 min, X-ray films were taken in a darkroom and the membrane was compressed to emit light; the results were obtained by developing and photographic fixing, and the results were analyzed using Quantity One Software from Bio-Rad company. The results were shown in FIG. 14 and FIG. 15. Compared with the control group in the figures, *P<0.05 and **P<0.01. FLU represents fluoxetine group.

Experimental results: compared with the blank control group, fluoxetine can significantly improve the expression of proteins MITF, tyrosinase (TYR), tyrosinase-related protein 1 (TRP-1) and tyrosinase-related protein 2 (TRP-2) in hair-removed synchronized skin hair follicles of C57BL/6 mice, and there was statistically significant difference.

Experimental conclusions: fluoxetine can increase the melanin content in hair follicles through improving the expression of proteins which are important for the melanin synthesis in the hair-removed synchronized skin hair follicles of C57BL/6 mice.

Figure 16:
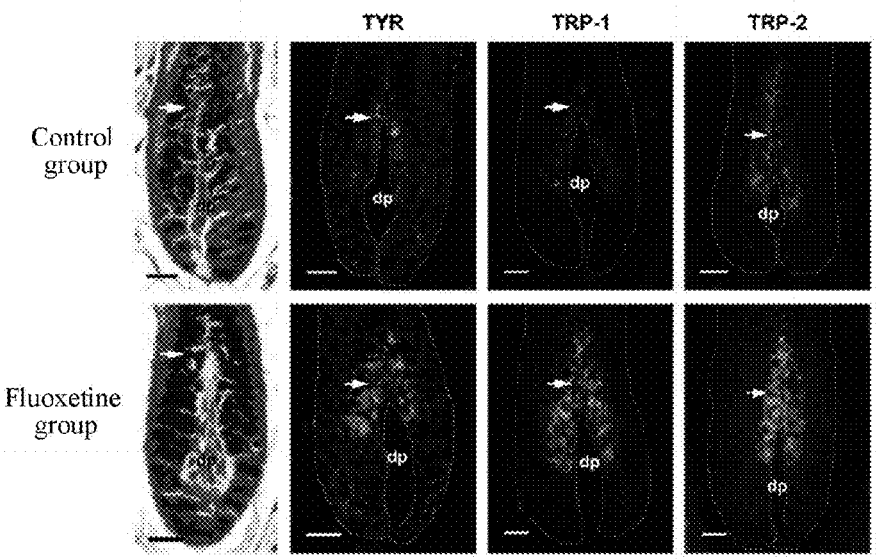
FIG. 16 shows the immunohistochemical results for the proteins which are important for the synthesis of hair follicle melanin of C57BL/6 mice.

3.3 Immunohistochemisty Assay for Detecting the Expression of Proteins which are Important for Melanin Synthesis in Hair Follicles of C57BL/6 Mice On the 12$^{th}$ day after administration, the animals were sacrificed, and skin samples were collected parallel to the spine line. Skin tissues were fixed in 10% formaldehyde for 48 h and embedded in paraffin, then sliced longitudinally along the hair follicles (4 μm), and HE staining and immunohistochemical staining were carried out respectively. HE staining: conventional hematoxylin-eosin staining. Immunohistochemical staining: the slices were dewaxed and hydrated, incubated with 3% hydrogen peroxide at room temperature for 10 min, washed with PBS for 5 min and repeated three times. A goat serum blocking solution was added dropwise for blocking for 20 min after heat-induced antigen retrieval, and rabbit-derived TYR, TRP-1 and TRP-2 antibody were added, and incubated at 4° C. overnight. TRITC-labeled goat anti-rabbit IgG was added after washing with PBS three times, incubated at 37° C. for 30 min and washed with PBS three times with each time for 5 min. An anti-fluorescent quencher was added and the slices were mounted. The diluted solutions of the primary antibodies were used to replace the primary antibodies to repeat the above processes, as a negative control experiment. Two skin slices were selected for each animal and five visual fields were randomly selected for each slice for photographing and recording with a fluorescence microscope. The results were shown in FIG. 16. The scale in the pictures are: 20 μm; dp, hair papilla.

Experimental results: as compared with the blank control group, fluoxetine can significantly improve the expression of proteins tyrosinase (TYR), tyrosinase-related protein 1 (TRP-1) and tyrosinase-related protein 2 (TRP-2) in the hair follicle melanocytes in hair-removed synchronized skin areas located above the hair papilla of C57BL/6 mice.

Experimental conclusions: fluoxetine can increase the hair follicle melanin content through improving the expression of proteins which are important for the melanin synthesis in the hair follicle melanocytes in hair-removed synchronized skin of C57BL/6 mice, which is identical with the Western Blotting result.

IV. Effects of Fluoxetine on Melanogenesis in Skin Tissues.

The beneficial effect of the fluoxetine on melanogenesis is not limited to skin of C57BL/6 mice or limited to hair follicular melanin. For example, it is found that fluoxetine can promote the recovery of pigments in the zebrafish depigmentation model induced by PTU.

4.1 Effects of Fluoxetine on Melanogensis in Zebrafish

Figure 17:
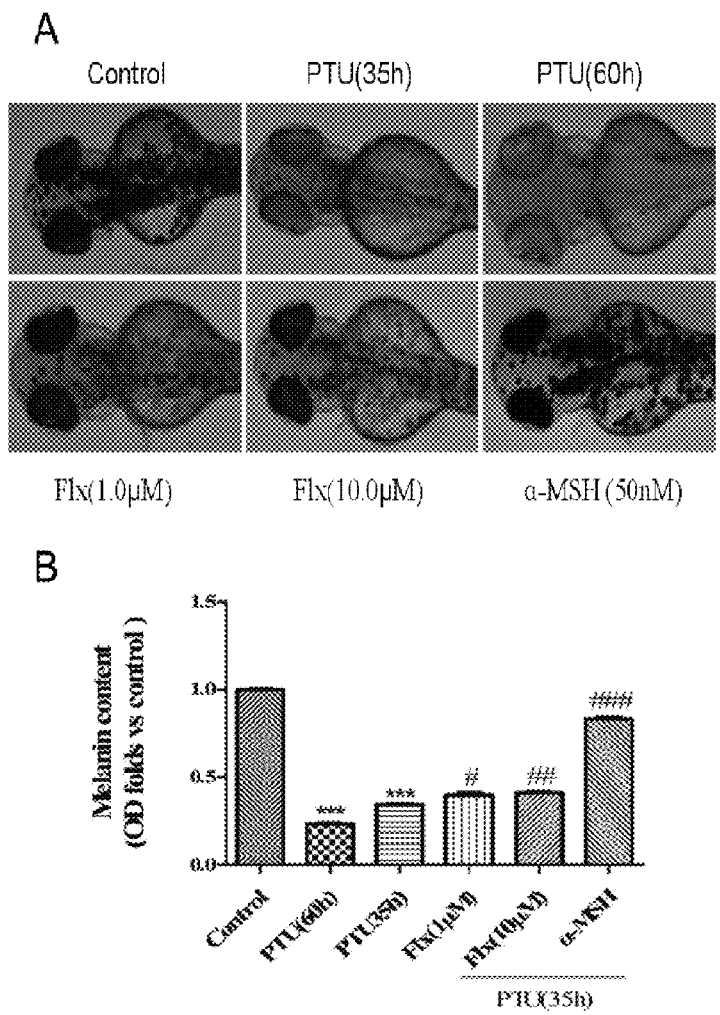
FIG. 17 shows the effect of fluoxetine on melanogenesis in zebrafish embryos.

Zebrafish in embryo and larvae stages is transparent and can be directly observed under stereoscope, which provides an opportunity to observe changes in melanin. FIG. 17 shows the effect of fluoxetine on melanogenesis in zebrafish. The zebrafish depigmentation model were obtained by treating zebrafish embryos with 1-phenyl 2-thiourea (PTU). Panel A shows zebrafish embryos observed under stereoscope. "Control" shows a normal zebrafish embryo without any treatment at 60 hours after fertilization. "PTU(35)" shows an embryo at 35 hours after fertilization and "PTU (60)" represents a zebrafish embryo at 60 hours after fertilization. Both embryos were treated in 0.2 mM ("M" stands for "mole/liter" throughout this disclosure) PTU to inhibit melanogenesis from after fertilization until the time their pictures were taken, i.e., at hour 35 and hour 60, respectively, i.e., the PTU(35) group and the PTU(60) group. "Flx(1.0 μM)" is a picture of embryo at 60 hours after fertilization. The embryo has been treated with 1.0 μM fluoxetine at 12 hours after fertilization. Likewise, "Flx(10.0 μM)" shows a picture of embryo taken at 60 hours after fertilization. Embryos in both "Flx(1.0 M)" and "Flx(10.0 μM)" embryo was first treated with 0.2 mM PTU from hour 6 to hour 35 after fertilization (i.e., PTU(35) group) and, in addition, treated with 10.0 μM fluoxetine from hour 12 to hour 60 after fertilization. "α-MSH(50 nM)" shows a PTU (35) group zebrafish embryo administered with α-Melanocyte-stimulating hormone at 50 nM from hour 12 to hour 60. Panel B shows the corresponding melanin contents. All data were expression for at least three experiments. ***P<0.001 vs control; #P<0.05, ##P<0.01, ###P<0.001 vs PTU (35 h) group. Data expressed as mean±SD (n=40).

As shown in FIG. 17, fluoxetine, even at a concentration of 1.0 μM fluoxetine, increased melanogenesis in the PTU model zebrafish, especially in its skin and eyes.

4.2 Effects of Fluoxetine on TYR Activities in Zebrafish

Figure 18:
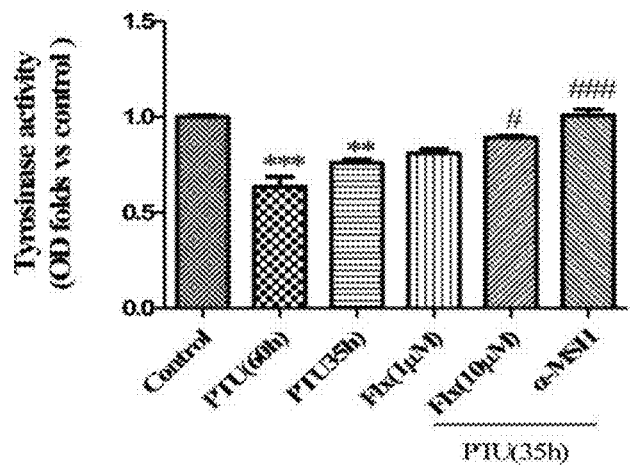
FIG. 18 shows the effect of fluoxetine on TYR activities in zebrafish.

Melanogenesis is one of the important functions of melanocytes, which is regulated by three enzymes—tyrosinase (TYR), tyrosinase-related protein-1 (TRP-1), and tyrosinase associated protein-2 (TRP-2). Among them TYR is the key and rate limiting enzyme. The activity of TYR in the PTU(35) group zebrafish by exposing the zebrafish to fluoxetine for 48 hours (i.e., from hour 12 to hour 60 after fertilization). The TYR activities are shown in FIG. 18, which indicates that fluoxetine treatment enhanced the TYR activity in the PTU(35) group zebrafish. Such effects appear to be dosage dependent in that Flx(10.0 μM) exhibited higher TRY activity than Flx(1.0 μM) did.

4.3 Effects of Fluoxetine on Melanogensis in In Vitro Human Skin Tissues

Figure 19:
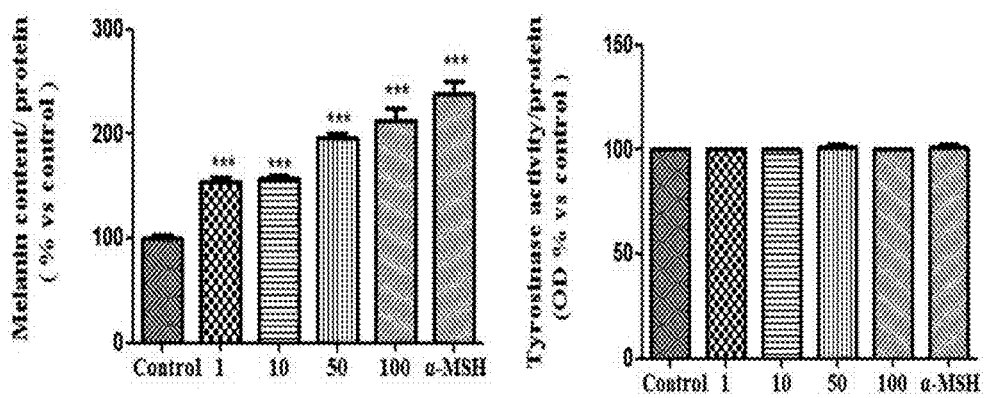
FIG. 19 shows the effect of fluoxetine on the melanogenesis in vitro culture normal human skin tissue.

Fluoxetine in the range of 1-100 μM were applied to in vitro cultured normal human skin tissue. Forty-eight (48) hours after administering fluoxetine, the melanin contents and the tyrosinase activities were obtained using the NaOH cracking process and L-DOPA. FIG. 19 clearly shows that fluoxetine stimulates melanogenesis in skin tissue at the concentration of 1 μM. On the other hand, the activity of tyrosinase did not exhibit any change in the same fluoxetine concentration range.

V. Effects of Fluoxetine Ointments.

Topical creams/ointments containing fluoxetine were tested for treating depigmentation model. In certain embodiments, fluoxetine ointments (i.e., creams or ointments that contains fluoxetine) contains fluoxetine at a mass concentration of 0.01% to 1.0% or more. The ointments further contains pharmaceutically acceptable carriers or solvents known in the art. In one embodiment, the 100 mL fluoxetine ointment contains: fluoxetine 10 mg, octadecanol 3.5 g, 1.5 g of white petrolatum, stearic acid 1.0 g, liquid paraffin 2.5 mL, 1.5 g glyceryl stearate, sodium lauryl sulfate 0.5 g, glycerol 2.5 mL, triethanolamine 0.2 mL, ethylparaben 50 μL, with the balance in ultra-pure water.

Figure 20:
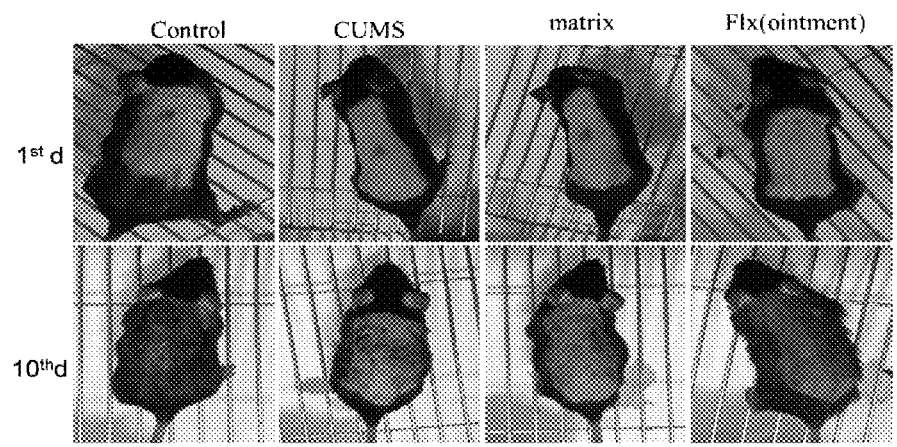
FIG. 20 shows the effect of fluoxetine ointment on the pigmentation of the dorsal skin in CUMS model C57BL/6 mice.

5.1 Effects of Fluoxetine Ointment on the Color of the Dorsal Skin in CUMS Model C57BL/6 Mice In order to investigate the effects of fluoxetine ointment on the melanogenesis of the dorsal skin in CUMS model C57BL/6 mice, the CUMS method was used to create the depigmentation model of the dorsal skin in C57BL/6 mice and the color of the dorsal skin in C57BL/6 mice was observed 12 days after applying the fluoxetine ointment. As shown in FIG. 20, the color of the dorsal skin in mice in the CUMS model group is significantly lighter than that in the normal group, and the color of the dorsal skin in mice in the group treated with the fluoxetine ointment is significantly darker than that in the model group.

Figure 21:
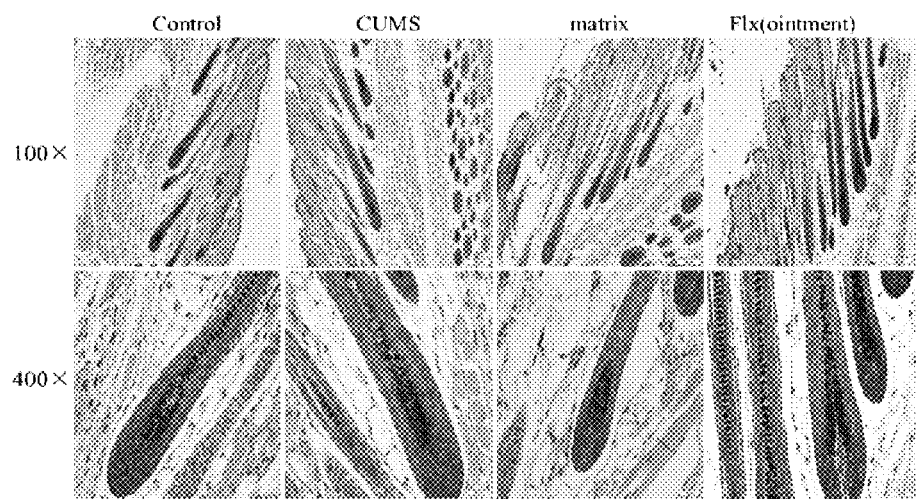
FIG. 21 shows the effect of fluoxetine ointment on the hair follicles HE staining of CUMS model C57BL/6 mice.

5.2 Effects of Fluoxetine Ointment on the Hair Follicles HE Staining of the Dorsal Skin in CUMS Model C57BL/6 Mice In order to further demonstrate that fluoxetine can restore the color of the dorsal skin in CUMS model C57BL/6 mice, skin tissues fixed with 4% paraformaldehyde for HE staining were examined. The results are shown in FIG. 21. The HE staining results of skin tissues in the model group and the matrix group show that melanosomes at hair follicle sites are reduced, and 12 days after administrating fluoxetine ointment, melanosomes in hair follicles are significantly increased. The results indicate that fluoxetine ointment can increase the number of melanosomes in hair follicles of the skin.

Figure 22:
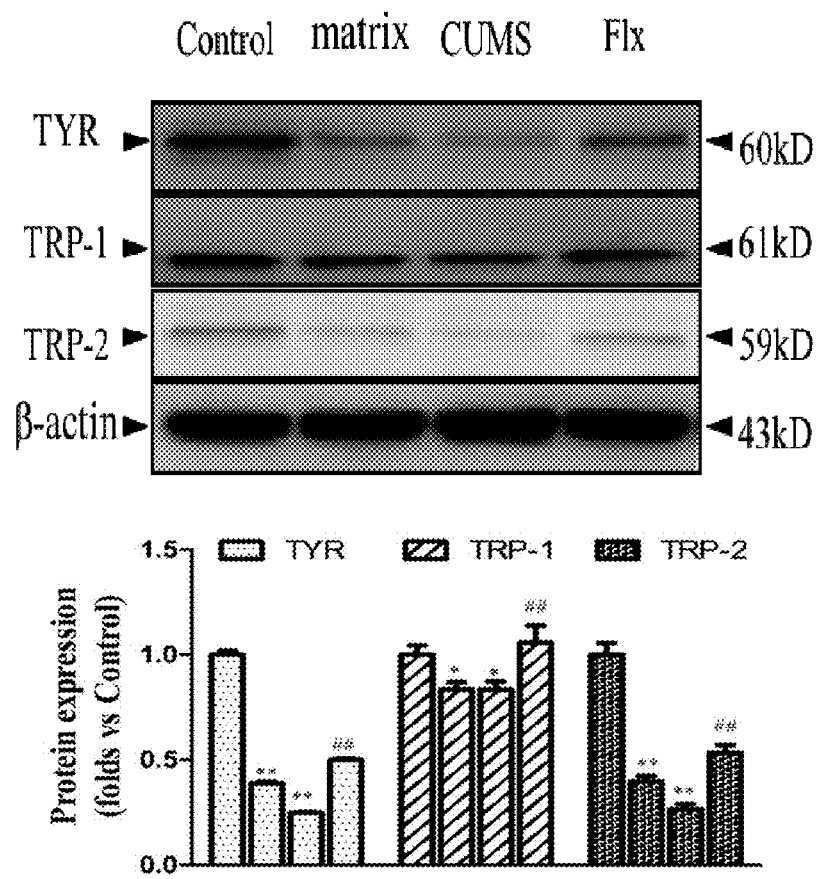
FIG. 22 shows the effect of fluoxetine ointment on the protein expression of TYR, TRP-1 and TRP-2 in dorsal skin of CUMS model C57BL/6 mice.

5.3 Effects of Fluoxetine Ointment on the Expression of TYR, TRP-1 and TRP-2 in the Dorsal Skin of CUMS Model C57BL/6 Mice Skin color is determined by melanocytes on the skin surface and melanin synthesized by melanocytes. Synthesis of melanin is mainly regulated by tyrosinase (TYR), tyrosinase-related protein-1 (TYR-1), and tyrosinase-related protein-2 (TYR-2). TYR is a key enzyme for melanomagenesis and a key protein for regulating melanomagenesis. Studies were carried out to examine whether fluoxetine has regulation effect on down-regulated protein expression of TYR, TRP-1 and TRP-2 in the dorsal skin of CUMS model-induced depigmentation model C57BL/6 mice. The results are shown in FIG. 22. According to FIG. 22, the CUMS model causes down-regulated protein expression of TYR, TRP-1 and TRP-2 in the dorsal skin of C57BL/6 mice, and there is no significant difference between the matrix group and the model group, proving that the blank matrix has no significant effects on the expression of melanin-related proteins. After the fluoxetine ointment treatment is administered, the expression of TYR, TRP-1 and TRP-2 in the dorsal skin of CUMS model C57BL/6 mice is significantly increased. It is demonstrated that fluoxetine promotes the synthesis of melanin possibly by increasing the expression of melanogenesis-related proteins.

Figure 23:
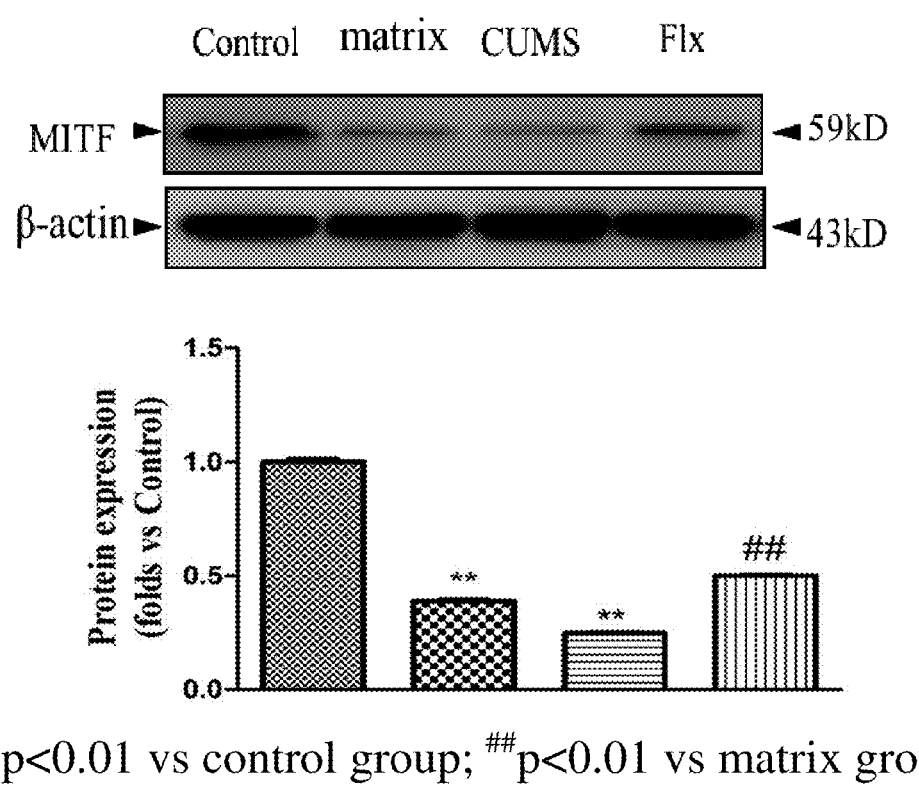
FIG. 23 shows the effect of fluoxetine ointment on the protein expression of MITF in dorsal skin of CUMS model C57BL/6 mice.

5.4 Effects of Fluoxetine Ointment on the Expression of MITF in the Dorsal Skin of CUMS Model C57BL/6 Mice MITF is an important regulating factor in melanogenesis, which regulates transcription and translation processes of TYR, and researches suggest that MITF activation can significantly regulate the expression of TYR and TRP-1, but has no significant effects on regulation of TRP-2. MITF activation can up-regulate the expression of TYR. Experiments were carried out to understand whether the fluoxetine ointment promotes the protein expression of MITF in the dorsal skin of CUMS model C57BL/6 mice. The results are shown in FIG. 23. According to FIG. 23, CUMS causes down-regulation in the expression of MITF in the dorsal skin of C57BL/6 mice, and fluoxetine ointment significantly increased the down-regulated level of MITF induced by CUMS. The results demonstrate that fluoxetine ointment increases melanogenesis, probably by up-regulating the expression of MITF to up-regulate the expression of TYR.

5.5 Effects of Fluoxetine Ointment on the Melanogenesis in Guinea Pig Skin.

Figure 24:
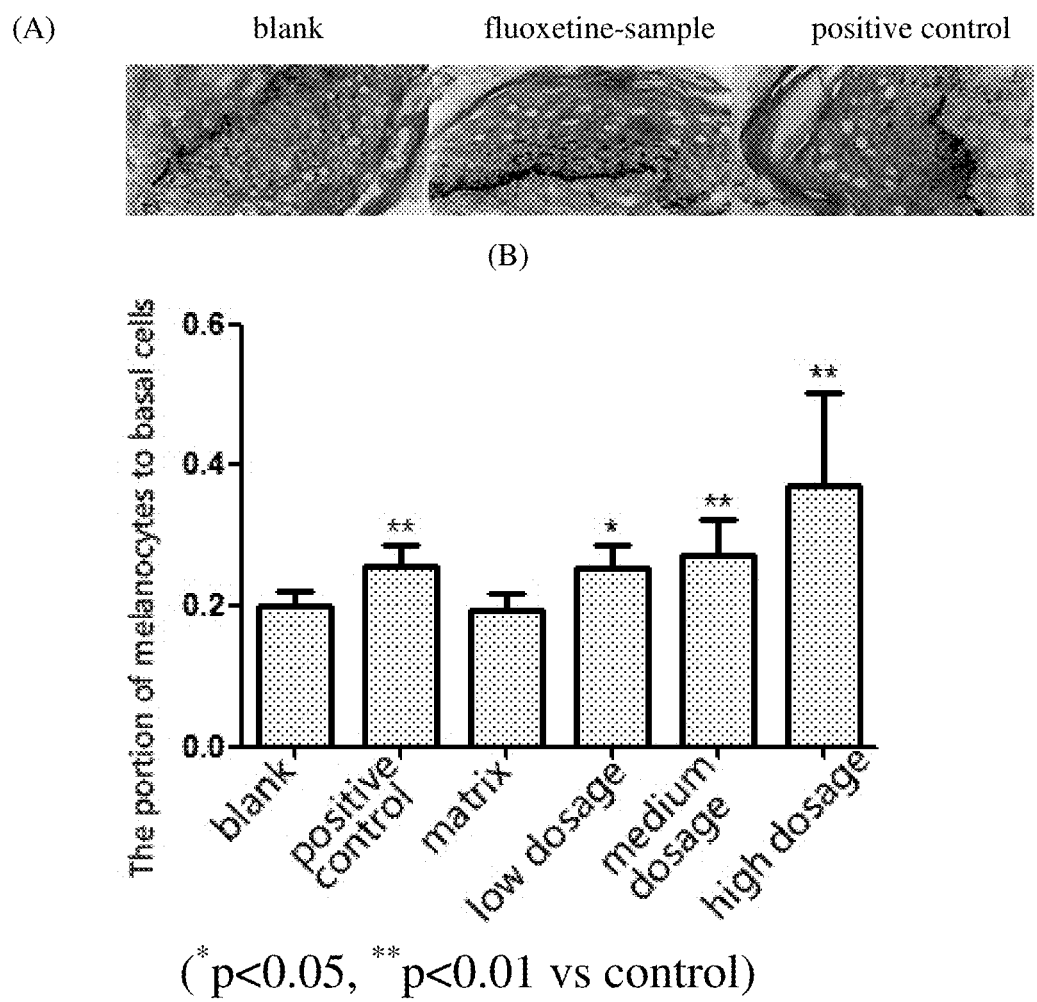
FIG. 24 shows the effect of fluoxetine ointment on melanogenesis in guinea pig skin.

In this experiment, fluoxetine ointments at low, medium, and high dosages (0.01% g/g, 0.1% g/g, and 1% g/g, respectively) were topically applied to the back skin of brown skinned guinea pigs once a day for twenty one (21) consecutive days. Tacrolimus was topically administered to serve as a positive control. Skin samples were collected. Immunohistochemical staining and DOPA staining were used to show effects of the fluoxetine ointment on melanocytes in skin basal cell. FIG. 24 compares sample from the blank control, the low, medium, and high dosages, and a positive control. The blank control is a sample without any treatment. The fluoxetine sample was treated with a fluoxetine ointment while the matrix sample was treated with the ointment without fluoxetine in it. Panel A shows pictures of a blank control sample, the sample using the fluoxetine ointment, and a positive control sample. It indicates that fluoxetine increased the concentration of melanin in the skin of the guinea pig as well as melanocytes in the basal layer.

Figure 25:
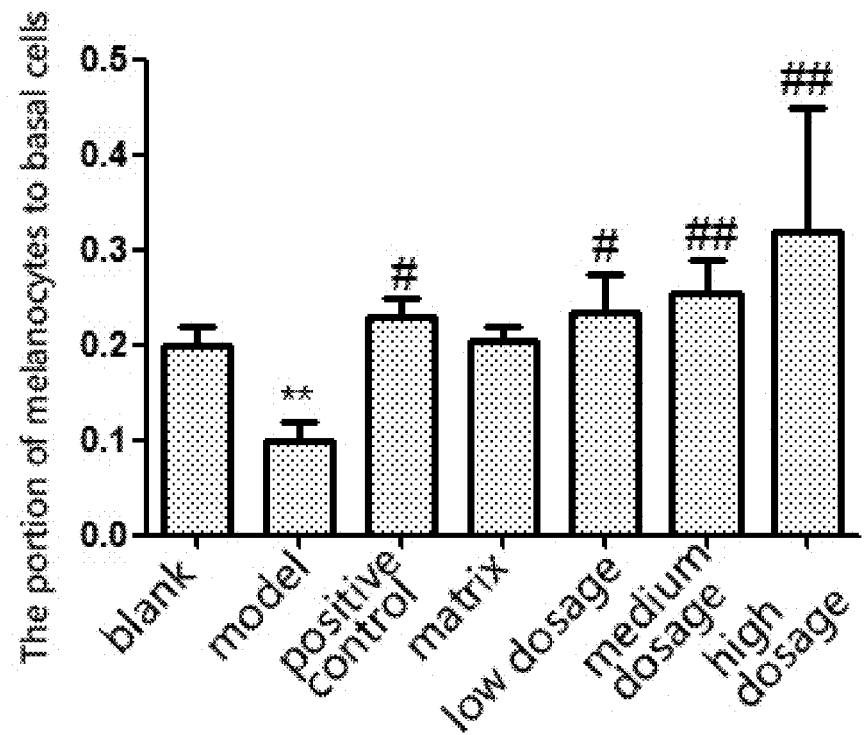
FIG. 25 shows the effect of fluoxetine ointment on melanogenesis in hydroquinone induced depigmentation model in guinea pig skin.

5.6 Effects of Fluoxetine Ointment on Melanogenesis in Hydroquinone Induced Depigmentation Model in Guinea Pig Skin In this experiment, a topical cream of 2.5% hydroquinone was applied topically to the skin of guinea pigs to obtain a model. After one week without administering the hydroquinone cream, the guinea pig model was administered topically fluoxetine ointments of low, medium and high doses (0.01% g/g, 0.1% g/g and 1% g/g, respectively) once a day for twenty one (21) consecutive days. A tacrolimus cream was used as the positive control. One day after the stopping administering the topical creams, skin samples of 1 cm×1 cm in size were collected at the center of the skin area where creams have been administered. Immunohistochemical staining and DOPA staining were used to show effects of the fluoxetine ointment on melanocytes in skin basal cell. FIG. 25 compares sample from the blank control, the model group, the positive control, matrix, the low, medium, and high dosages. It shows that fluoxetine, even at the low dosage of 0.01%, increased the melanocytes in a dosage dependent fashion.

What is claimed is:

1. A method for treating a depigmentation disease in a mammal, comprising administering an effective amount of fluoxetine to a mammal in need thereof, wherein the fluoxetine is administered topically to a skin surface of the mammal in form of an ointment comprising fluoxetine,
   wherein the depigmentation disease non-segmental is vitiligo and the mammal is not suffering from leukotrichia,
   wherein the ointment is administered once or more a day;
   wherein 100 mL fluoxetine ointment consists of: 10 mg fluoxetine, 3.5 g octadecanol, 1.5 g of white petrolatum, stearic acid 1.0 g, liquid paraffin 2.5 mL, 1.5 g glyceryl stearate, sodium lauryl sulfate 0.5 g, glycerol 2.5 mL, triethanolamine 0.2 mL, ethylparaben 50 µL, with the balance in ultra-pure water.

2. The method according to claim 1, wherein fluoxetine promotes expressions of MITF, tyrosinase (TYR), and tyrosinase-related protein 1 (TRP-1).

3. The method according to claim 1, wherein fluoxetine enhances the activity of tyrosinase.

* * * * *